United States Patent [19]

Bombardelli et al.

[11] Patent Number: 5,166,139

[45] Date of Patent: Nov. 24, 1992

[54] COMPLEXES OF SAPONINS AND THEIR AGLYCONS WITH PHOSPHOLIPIDS AND PHARMACEUTICAL AND COSMETIC COMPOSITIONS CONTAINING THEM

[75] Inventors: Ezio Bombardelli; Gianfranco Patri; Roberto Pozzi, all of Milan, Italy

[73] Assignee: Indena, S.p.A., Milan, Italy

[21] Appl. No.: 643,791

[22] Filed: Jan. 18, 1991

Related U.S. Application Data

[63] Continuation-in-part of Ser. No. 514,126, Apr. 25, 1990, abandoned, which is a continuation of Ser. No. 158,577, Feb. 22, 1988, abandoned.

[30] Foreign Application Priority Data

Feb. 26, 1987 [IT] Italy ................ 19496 A/87

[51] Int. Cl.⁵ ................ A61K 31/665; A61K 31/705; A61K 9/127
[52] U.S. Cl. ................ 514/26; 514/33; 514/35; 514/887; 536/5; 536/17.1; 536/18.1; 536/18.2; 536/55.1; 536/117; 424/450; 424/401; 554/80; 554/224
[58] Field of Search ................ 514/26, 33, 35, 887; 424/450, 401; 536/5, 17.1, 18.1, 18.2, 55.1, 117; 260/403

[56] References Cited

U.S. PATENT DOCUMENTS

| | | | |
|---|---|---|---|
| 4,101,652 | 7/1978 | Bonati | 536/5 |
| 4,335,113 | 6/1982 | Combier et al. | 514/26 |
| 4,624,919 | 11/1986 | Kokusho et al. | 536/4.1 |

FOREIGN PATENT DOCUMENTS 0462710 1/1950 Canada .
0142193 5/1985 European Pat. Off. .
0283713 9/1988 European Pat. Off. .
1217547 5/1966 Fed. Rep. of Germany .
62-238299 10/1987 Japan .

OTHER PUBLICATIONS

Assa et al.; Biochem. Biophys. ACTA 307:83–91 (1973).
Elias et al.; J. Histochem. Cytochem. 27(9):1247–1260 (1979).
Nakamura et al.; Chem. Pharm. Bull. 29(6):1681–1688 (1981).
Yu et al.; Chem.–Biol. Interactions 52:185–202 (1984).
Higuchi et al.; Phytochemistry 27(4):1165–1168 (1988).
Chirua et al.; Chemical Abstracts 81:120925z (1974).
Krokhmalyuk et al.; Chemical Abstracts 84:74569y (1976).
Proserpio et al.; Cosmetics & Toiletries; 6–7, 10–11, 14, May 1988.

Primary Examiner—Ronald W. Griffin
Assistant Examiner—Nancy S. Carson
Attorney, Agent, or Firm—Bucknam and Archer

[57] ABSTRACT

Complexes of saponins from *Centella asiatica*, *terminalia sp.* and *Terminalia sericea* and relevant aglycons with phospholipids are described. The saponins may be asiaticoside, madecassicoside and sericoside. The molar ratio of phospholipids to saponins is from 0.5 to 2. The phospholipids are selected from the group consisting of soy lecithins, phospholipids from bovine or swine brain or cutis, phosphatidylcholine, phosphatidylserine, phosphatidylethanolamine in which the acyl groups can be the same or different and are mostly derived from palmitic, stearic, oleic, linoleic, linolenic acids. Pharmaceutical compositions and the method of treatment are also described.

6 Claims, No Drawings

COMPLEXES OF SAPONINS AND THEIR AGLYCONS WITH PHOSPHOLIPIDS AND PHARMACEUTICAL AND COSMETIC COMPOSITIONS CONTAINING THEM

This application is a continuation-in-part of U.S. Ser. No. 514,126, filed Apr. 25, 1990, now abandoned, which is a Continuation of U.S. 158,577 filed Feb. 22, 1988, now abandoned, the priority of which is claimed under 35 U.S.C. 120.

The present invention relates to complexes of saponins and relevant aglycons, obtained from *Centella asiatica* and *Terminalia sp.*, with phospholipids, to a process for the preparation thereof and to pharmaceutical and/or cosmetic compositions containing them. *Centella asiatica* saponins (asiaticoside and madecassicoside) and sericoside from *Terminalia sericea* are used individually or as a mixture. These saponins have the sugar units bound to carboxylic groups by means of an ester type bond and are therefore structurally different from the other known saponins (e.g. aescin) where the sugar units are bound to hydroxy groups with an ether type bond.

The present invention relates to complexes of these saponins, single and as a mixture, with phospholipids.

The present invention relates also to complexes of the aglycons derived from the above mentioned saponins, with phospholipids. *Centella asiatica* saponins and aglycons thereof and sericoside from *Terminalia sericea* are endowed with antiinflammatory, vasotonic, vasoprotecting, antiulcer and antiedema properties which allow their use in pharmaceutical and/or cosmetic field. Now it has surprisingly been found that complexes of *Centella asiatica* saponins and aglycons thereof and of sericoside from *Terminalia sericea* with phospholipids are endowed with better pharmacological activity and tolerability than the individual components. In addition, an effective absorption by topical route, due to the lipophilic characteristic, is attained.

The phospholipids that can be used according to this invention may be either vegetal or synthetic in nature, with acyl residues being the same or different, as shown by the formula:

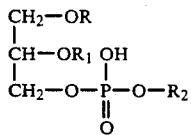

where R and $R_1$, which are the same or different, are mostly acyl residues of the palmitic, stearic, oleic, linoleic, linolenic acids, while $R_2$ is the residue of choline, phosphatidyl ethanolamine or serine.. Particularly preferred phospholipids for use in cosmetics are the vegetal or naturally occurring phospholipids, such as those obtained from soy or from bovine or swine cutis or brain, similar to the ones that are found in human dermis; for other uses, a phospholipid which is chemically homogeneous and defined in its structure units (acyl and phosphoryl-amine groups) is preferred.

The complexes according to the invention are prepared by reacting the individual saponins, their mixture and their mixture with the relevant aglycons with the phospholipids in an aprotic solvent. The molar ratios of the phospholipid/saponins are in the range of from 0.5 to 2, more preferably about 1.

After solubilization has been completed, the complex compounds are isolated by removing the solvent under vacuum, by freeze drying or by precipitation with nonsolvents.

The thus obtained complexes are lipophilic in character and soluble in apolar and aprotic solvents, in which the individual components of the complex are normally insoluble.

The formation of a molecular complex is confirmed by a NMR spectroscopy study of the proton, carbon-13 and phosphorus, by comparing the spectra of the individual constituents with those of the reaction product. In the $^1$H-NMR spectrum of the complexes, the signals from the protons of the lipid chain are well evident, as well as a broadening of the band of N-(Me)$_3$ group of choline, showing that this moiety is involved in the complex compound.

In the $^{13}$C-NMR spectrum, the value of the relaxation times of the nuclei that are most involved in the complex's formation is reduced in a similar manner to the proton spectrum discussed hereinabove, until disappearance of all the signals characteristic of the terpene moiety of the saponin takes place. In the $^{31}$P-NMR spectrum, a substantial broadening of the phosphorus band is observed with an evident peak shift. From these data, it can be deduced that, in the formation of the complex compound, the saponin is bound to the phospholipid by engagement with the polar head of this latter; the lipophilic character is imparted upon the complex compound by the lipid chains, which can freely rotate in the medium, as it can be deduced from their H-NMR spectrum, which shows no changes. The complexes prepared according to the invention were tested pharmacologically: the complexed forms prove to be more active than the corresponding free or partially complexed forms.

Table 1 shows the results obtained in the healing of wounds in rats treated s.c. with prednisone (0.5 mg/mg/rat/die) in the test according to Morton et al., *Arch. int. Pharmacodyn.* 196, 177 (1972) appears that a cream containing 2% of a complex of soy-bean/phospholipids with *Centella asiatica* selected triterpenes is more active than the free *Centella asiatica* selected triterpenes (standardized mixture containing 40% asiaticoside and 30% each of asiatic and madecassic acid). Table 2 shows the results obtained in the Croton oil test on the rat with the complex sericoside/distearoylphosphatidylcholine in comparison with the components. In this case too the complex is more active: the same antiinflammatory activity is obtained with half the dose (0.25 uM/ear for the complex and 0.50 uM/ear for the free sericoside respectively).

From the point of view of pharmaceutical and cosmetic technology, the complexes obtained as above can be employed as microdispersions in water by preparing them by homogenization using high-speed stirrers or ultrasonic procedures, or they may be incorporated as such into appropriate pharmaceutical or cosmetic preparations.

For topical administration, it is convenient to use the above mentioned microdispersions, which may optionally be added with thickening agents, said microdispersions can contain very wide percentages of active ingredient, from 0.1 to 30%, and may also be incorporated in forms of gels or emulsions for dermatologic or cosmetic purposes, or used as themselves as above mentioned.

The complexes, due to their high lipophilia, may be dissolved in oils, in which they are stable, or incorporated in water/oil emulsions, or may be used in the preparation of capsules, tablets or suppositories.

In the preparation of the pharmaceutical compositions, care must be taken in using solvents, some of which, for examples alcohols and those having a high dielectric constant, such as dimethylsulfoxide, cleave the complexes, as evidenced by NRM spectroscopy. In fact, complexes dissolved in said solvents show spectra which substantially correspond to the summatory of spectra separately registered for the single constituents.

Therefore, in the formulations the compatibility of the compound with the dispersing medium must be taken into account, in order to safeguard complex stability and consequently activity. Advantageously, in view of the higher activity of the complexed forms according to the invention, the active ingredient dosage may, under certain circumstances, be reduced, the specific activity remaining unchanged.

Suitable forms for pharmaceutical and/or cosmetic uses by topical application, are creams, gels or aqueous microdispersions containing 0.1 to 30% by weight of the complexes. These forms will be administered one or several times daily, depending on the intended use. Suitable forms for pharmaceutical uses, by oral administration, are tablets, capsules, syrups, granules, solutions, which contain unit doses of the complexed active principle in the range from 1 to 500 mg. These pharmaceutical forms will be administered once or several times a day, depending on the severity of the pathology to be treated and the patient conditions.

The compositions according to the invention can in particular be used for treating conditions of inflammation, altered capillary fragility and permeability and, in general in all the fields in which an activity of the active free component is recognized at present.

EXAMPLE 1

Preparation of the complex of sericoside with distearoylphosphatidylcholine 3.3 g of sericoside were suspended in 10 ml of methylene chloride and added with 4 g of distearoylphosphatidylcholine. The suspension was heated for some minutes, until complete dissolution, then the solution was concentrated to small volume. The residue was taken up in 30 ml of n-hexane; a white precipitate formed which, upon filtration and drying, had m.p. 144°-146° C. and $[\alpha]_D + 9.9°$ (c=0.5 CHCl$_3$/MeOH 1:1).

EXAMPLE 2

Preparation of the complex of a terpene fraction prepared from Centella asiatica with soy phosphatidylcholine 8 g of a mixture consisting of 40% asiaticoside, 30% of asiatic acid and 30% of madecassic acid, were dissolved in 50 ml of dioxane, together with 9 g of soy phosphatidylcholine (titre 95%). The resulting solution was freezedried. 16.5 g of the complex of saponins with triterpene acids were obtained, whose solubility and spectroscopic data were in agreement with the complex. M.p. of the complex 182°-186° C.

EXAMPLE 3

Preparation of the complex of asiaticoside with distearoylphosphatidylcholine 9.5 g of asiaticoside were suspended in 50 ml of methylene chloride and 9 g of distearoylphosphatidylcholine (titre 99.9%) was added. The suspension was heated to mild reflux until complete dissolution. The chloromethylene solution was concentrated to small volume and poured into 200 ml of n-hexane. After filtration and drying, 17.5 g of a white powder having spectroscopic characteristics in agreement and m.p. 187° C. and $[\alpha]_D + 2$ (c=0.25 CHCl$_3$/MeOH 1:1).

TABLE 1

Skin wounds on the rat treated s.c. with prednisone (0.5 mg/ml/rat/die)

| Substances (in brackets No. animals | Dose mg/rat | Wounds area (M ± SE) mm², at day | | | |
|---|---|---|---|---|---|
| | | 0 | 1 | 2 | 3 |
| Controls (12) | — | 315.56 ±3.17 | 296.54 ±7.56 | 280.09 ±9.53 | 264.61 ±10.82 |
| CAST*/ DSPC** (12) | 4 | 315.65 ±4.52 | 283.00 ±8.57 (−4.6) | 254.16 ±8.56 (−9.25) | 225.28 ±6.63 (−14.86)** |
| CAST* (12) | 4 | 315.61 ±3.83 | 294.14 ±7.12 (−1) | 271.55 ±8.47 (−3) | 245.11 ±9.78 (−4) |

**p<0.01 Dunnett t test
*CAST Centella asiatica selected triterpenes
**DSPC Distearoylphosphatidylcholine

TABLE 2

Anti-oedema effect of tested substances at 6 h (Croton oil dermatitis in the mice ear, Tubaro et al., Agents Actions 17, 347, 1985)

| Substances | μM/ear | Animal used | Oedema mg M ± SE | Percent reduction |
|---|---|---|---|---|
| Controls | | 40 | 7.2 ± 0.2 | — |
| Sericoside/DSPC° | 1 | 28 | 0.7 ± 0.1 | 90.3* |
| | 0.5 | 14 | 0.8 ± 0.2 | 88.9* |
| | 0.25 | 14 | 3.9 ± 0.5 | 45.0* |
| Sericoside | 0.5 | 14 | 3.95 ± 0.45 | 46.1* |
| DSPC° | 0.5 | 14 | 6.5 ± 0.3 | 9.7 |
| Indomethacin | 0.5 | 14 | 1.8 ± 0.2 | 75.1* |

*p<0.05 variance analysis
°DSPC distearoylphosphatidylcholine

We claim:

1. A complex of a saponin which is derived from Centella asiatica, Terminalia sp. or Terminalia sericea wherein said saponin is asiaticoside, madecassicoside or sericoside or a mixture thereof with a phospholipid wherein the molar ratio of phospholipid to said saponin is 0.5-2.

2. The complex according to claim 1, wherein the molar ratio of said phospholipid to said saponin is about 1.

3. The complex according to claim 1, wherein the phospholipid is a member selected from the group consisting of soy lecithins, phospholipids from bovine or swine brain or cutis, phosphatidylcholine, phosphatidylserine and phosphatidylethanolamine, said phospholipid having acyl groups which are the same or different and which are derived from an acid consisting of palmitic, stearic, oleic, linoleic, and linolenic acids.

4. A pharmaceutical composition comprising as the active ingredient 0.1 to 30% by weight of the complex of claim 1 and a pharmaceutically acceptable diluent or carrier.

5. The complex according to claim 3, wherein the phospholipid is distearoylphosphatidylcholine and the saponin is 1) sericoside; 2) or mixture consisting of 40% asiaticoside, 30% of asiatic acid and 30% of madecassic acid, or 3) asiaticoside.

6. A method for producing an anti-inflammatory effect in a living subject which consists of administering to said living subject in need of treatment an anti-inflammatory effective amount of a composition containing 0.1-30% of the complex according to claim 1.

* * * * *